United States Patent [19]
Ashton et al.

[11] Patent Number: 5,436,259
[45] Date of Patent: Jul. 25, 1995

[54] SUBSTITUTED 1,2,4-TRIAZOLIN-3-ONE COMPOUNDS BEARING ACIDIC FUNCTIONAL GROUPS AS BALANCED ANGIOTENSIN II ANTAGONISTS

[75] Inventors: Wallace T. Ashton, Clark; Prasun K. Chakravarty, Edison; Linda L. Chang, Wayne, all of N.J.

[73] Assignee: Merck & Co., Inc., Rahway, N.J.

[21] Appl. No.: 154,883

[22] Filed: Nov. 18, 1993

Related U.S. Application Data

[63] Continuation-in-part of Ser. No. 970,360, Nov. 2, 1992, Pat. No. 5,281,614, which is a continuation-in-part of Ser. No. 875,038, May 1, 1992, abandoned, which is a continuation-in-part of Ser. No. 698,505, May 10, 1991, abandoned.

[51] Int. Cl.⁶ ..................... A61K 31/41; C07D 249/12
[52] U.S. Cl. ..................... 514/384; 514/359; 548/262.8; 548/263.2; 548/264.6
[58] Field of Search ............... 548/263.2, 264.6, 262.8; 514/359, 384

[56] References Cited

FOREIGN PATENT DOCUMENTS 0323841 7/1989 European Pat. Off. .
0400974 12/1990 European Pat. Off. .
0409332 1/1991 European Pat. Off. .
0412594 1/1991 European Pat. Off. .
0475898 3/1992 European Pat. Off. .
WO92/20662 11/1992 WIPO .

OTHER PUBLICATIONS

07/698,505 Chakravarty, et al. May 10, 1991.
07/875,038 Chakravarty, et al. May 01, 1992.
07/970,360 Chakravarty, et al. Nov. 02, 1992.

*Primary Examiner*—Yogendra N. Gupta
*Attorney, Agent, or Firm*—Valerie J. Camara; Mark R. Daniel; Joseph F. DiPrima

[57] ABSTRACT

Novel substituted 1,2,4-triazolin-3-ones of the formula (I) are useful as angiotensin II antagonists.

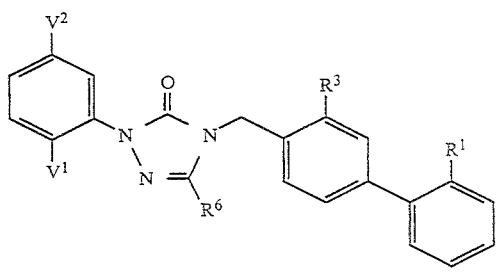

6 Claims, No Drawings

SUBSTITUTED 1,2,4-TRIAZOLIN-3-ONE COMPOUNDS BEARING ACIDIC FUNCTIONAL GROUPS AS BALANCED ANGIOTENSIN II ANTAGONISTS

RELATED APPLICATION

The present patent application is a continuation-in-part of application Ser. No. 07/970,360, filed 2 Nov. 1992, now U.S. Pat. No. 5,281,614, (allowed), which is a continuation-in-part of Ser. No. 07/875,038, filed 1 May 1992, now abandoned, which is a continuation-in-part of Ser. No. 07/698,505, filed 10 May 1991, abandoned.

INTRODUCTION OF THE INVENTION

This invention relates to novel substituted 1,2,4-triazolin-3-one compounds and derivatives thereof which are useful as angiotensin II antagonists in the treatment of elevated blood pressure and congestive heart failure. The substituted triazolinone compounds of the invention are also useful to reduce elevated intraocular pressure and to inhibit restenosis.

It also relates to processes for preparing the novel compounds; pharmaceutical formulations comprising one or more of the compounds as active ingredient; and, a method of treatment of hypertension, congestive heart failure, and elevated intraocular pressure.

The compounds of this invention also have central nervous sytem (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

BACKGROUND OF THE INVENTION

The renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the primary effector hormone of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption [M. Antonaccio. Clin..Exp. Hypertens. A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598;: 4,576,958; 4,582,847 and 4,880,804 in European Patent Applications 028,834; 245,637; 253,310; 291,969; 392,317; 399,731; 403,158; 403,159; 407,342; 411,507; 412,848; and 415,886; and in articles by A. T. Chiu, et al. [*Eur. J. Pharm. Exp. Therap*, 157, 13–21 (1988)] and by P. C. Wong, et. al. [*J. Pharm. Exp. Therap*, 247, 1–7(1988), *Hypertension*, 13,489–497 (1989)]. European Patent Applications 028,834 and 253,310 and the above three articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

This invemion relates to novel substituted 1,2,4-triazolin-3-one compounds and derivatives thereof which are useful as angiotensin II antagonists, primarily as antihypertensives. The compounds of this invention have the general formula (I):

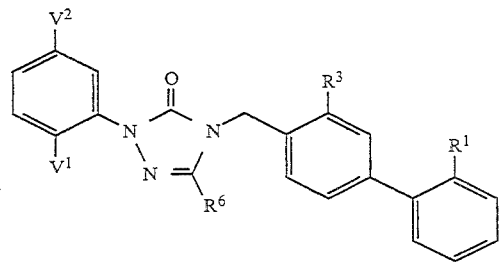

or a pharmaceutically acceptable salt thereof, wherein:

$R^1$ is —$SO_2NHCO_2R^{22}$, wherein $R^{22}$ is branched chain $C_3$–$C_4$ alkyl;

$R^3$ is (a) H, or (b) Cl, Br, I, or F;

$R^6$ is straight chain $C_1$–$C_2$ alkyl;

$V^1$ is Cl, Br, or $CF_3$;

$V^2$ is (a) —$(CH_2)_tNR^{21}COR^{22}$, wherein t is 0; $R^{21}$ is H; and $R^{22}$ is phenyl, $C_1$–$C_4$ alkyl or $C_1$–$C_2$ alkyl substituted with methoxy or ethoxy; or (b) —$CONR^{21}R^{22}$, wherein $R^{21}$ is H; and $R^{22}$ is $C_1$–$C_4$ alkyl.

One embodiment of the compounds of Formula 1 are those wherein

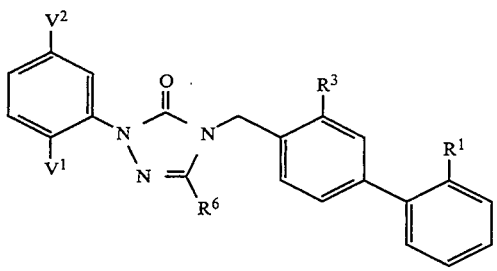

or a pharmaceutically acceptable salt thereof, wherein:
R[1] is —SO$_2$NHCO$_2$R$_{22}$, wherein R$^{22}$ is isopropyl or tert-butyl;
R[3] is H, or F;
R[6] is C$_1$–C$_2$ alkyl;
V[1] is Cl, Br, or CF$_3$;
V[2] is
(a) —NHCOR[22], wherein R[22] is phenyl, C$_1$–C$_4$ alkyl or C$_1$–C$_2$ alkyl substituted with methoxy or ethoxy; or
(b) —CONHR[22], wherein R[22] is C$_1$–C$_4$ alkyl.

This embodiment is exemplified by the following table:

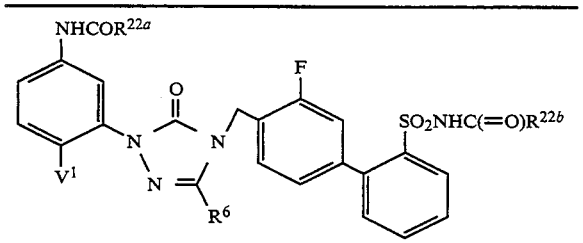

| R$^{22a}$ | R[6] | V[1] | R$^{22b}$ |
| --- | --- | --- | --- |
| phenyl | ethyl | Br | O-t-butyl |
| ethyl | ethyl | Br | O-t-butyl |
| n-butyl | ethyl | Br | O-t-butyl |
| ethyl | ethyl | Cl | O-t-butyl |
| methyl | ethyl | Cl | O-t-butyl |
| phenyl | ethyl | Cl | O-t-butyl |
| ethoxymethyl | ethyl | Br | O-t-butyl |
| ethoxymethyl | ethyl | Cl | O-t-butyl |
| n-butyl | ethyl | Cl | O-t-butyl |
| 2-methoxyethyl | ethyl | Br | O-t-butyl |
| n-butyl | ethyl | Br | O-i-propyl |
| n-butyl | ethyl | CF$_3$ | O-t-butyl |
| n-butyl | methyl | Br | O-t-butyl. |

This embodiment is exemplified further by the table below:

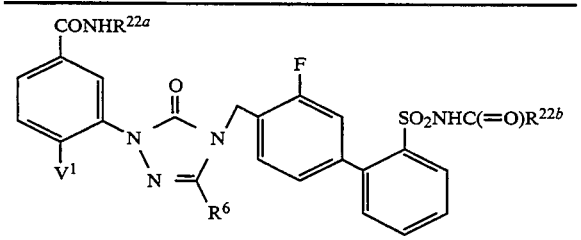

| R$^{22a}$ | R[6] | V[1] | R$^{22b}$ |
| --- | --- | --- | --- |
| n-butyl | ethyl | CF$_3$ | O-t-butyl |
| n-butyl | ethyl | Br | O-t-butyl |
| ethyl | ethyl | Br | O-t-butyl |
| ethyl | ethyl | Cl | O-t-butyl |

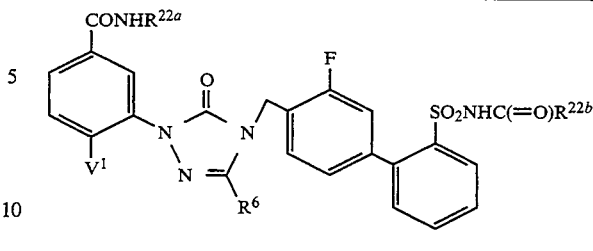

| R$^{22a}$ | R[6] | V[1] | R$^{22b}$ |
| --- | --- | --- | --- |
| methyl | ethyl | Cl | O-t-butyl |
| n-butyl | ethyl | Cl | O-t-butyl |
| n-butyl | ethyl | Br | O-i-propyl |
| n-butyl | methyl | Br | O-t-butyl. |

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

Compounds of Formula I may be prepared as described in U.S. Pat. No. 5,281,614 issued Jan. 25, 1994, the related PCT application, WO 92/20662, published 26 Nov. 1992, as well as the schemes illustrated below.

| | ABBREVIATIONS USED IN SCHEMES AND DISCUSSION |
| --- | --- |
| DMAP | Dimethylaminopyridine |
| DPPA | Diphenylphosphorylazide |
| DMF | Dimethylformamide |
| DBU | 1,8-Diazabicyclo[5.4.0]undecane |
| FAB MS | Fast Atom bombardment mass spectroscopy |
| THF | Tetrahydrofuran |
| DMSO | Dimethylsulfoxide |
| EtOAc | Ethyl acetate |
| HOAc | Acetic Acid |
| TFA | Trifluoroacetic acid. |
| BOP | Benzotriazol-1-yloxytris(dimethylamino)-phosphonium hexafluorophosphate |
| BOC | t-Butoxycarbonyl |
| Me | Methyl |
| Et | Ethyl |
| Bu | Butyl |
| Ph | Phenyl |
| aq. | Aqueous |
| cat. | Catalytic |

Scheme 1 illustrates the synthesis of compounds of formula (I) wherein V[1] is Cl or Br and V[2] is NHCOR[22]. The triazolinone intermediate 4 is synthesized by the general method described by L. Maravetz, U.S. Pat. No. 4,705,557 (1987) and G. Theodoridis, International Patent Application WO87/03782. The 2-halo-5-nitrophenylhydrazine 1 [generated from the hydrochloride, which is prepared from the 2-halo-5-nitroaniline according to H. Stroh and G. Westphal, Chem. Ber., 96, 184 (1963), by partitioning between diethyl ether and 1N sodium carbonate] is condensed with an α-keto acid 2 in aqueous acetic acid. The resulting hydrazone derivative 3 is heated in toluene with diphenylphosphoryl azide and triethylamine at a temperature up to 115° C. to yield the triazolinone 4. Separately, reaction of benzenesulfonyl chloride 5 with t-butylamine according to the procedure of J. G. Lombardino, J. Org. Chem., 36, 1843 (1971) yields the sulfonamide 6. Based on a literature method [M. J. Sharp, W. Cheng, and V. Snieckus, *Tetrahedron Lett.*, 28, 5093 (1987)], metalation ortho to the sulfonamide is achieved with n-butyllithium in THF at −40° to 0° C. Then treatment with triisopropyl borate followed by acidic work-up affords the boronic acid 7. This tradergoes cross-coupling with 4-bromo-2-fluorotoluene in the presence of tetrakis(triphenylphosphine)palladium(0) according to literaure methods [M. J. Sharp, op. cit.; N. Miyamura, T. Yanagi, and A. Suzuki, Synth, Commun., 11, 513 (1981)] to give a biphenyl product. α-Bromination by use of bromine in carbon tetrachloride at reflux under irradiation with light yields the bromomethyl derivative 8. Treatment of the triazolinone 4 with sodium hydride in DMF followed by the biphenylmethyl bromide 8 yields the N4-alkylated triazolinone 9. Reduction of the nitro group with stannous chloride in the presence of concentrated aqueous hydrochloric acid and THF, followed by a sodium hydroxide work-up, provides the amine 10. Reaction of 10 with an appropriate acid chloride $R^{22}COCl$ in pyridine in the presence of DMAP affords the amide derivative 11. Alternatively, 11 is obtained by coupling the amine 10 with the carboxylic acid $R^{22}CO2H$ in the presence of BOP reagent in methylene chloride. Next, the t-butyl protecting group is removed with amhydrous trifluoroacetic acid in the presence of anisole. The resulting sulfonamide is treated with sodium hydride in THF or DMF and then with di-t-butyl dicarbonate to yield the t-butyl sulfonylcarbamate 12. In a variation of the last step, di-t-butyl dicarbonate can be replaced by a branched $C_3$–$C_4$ alkyl chloroformate to provide the corresponding branched $C_3$–$C_4$ alkyl sulfonylcarbamate.

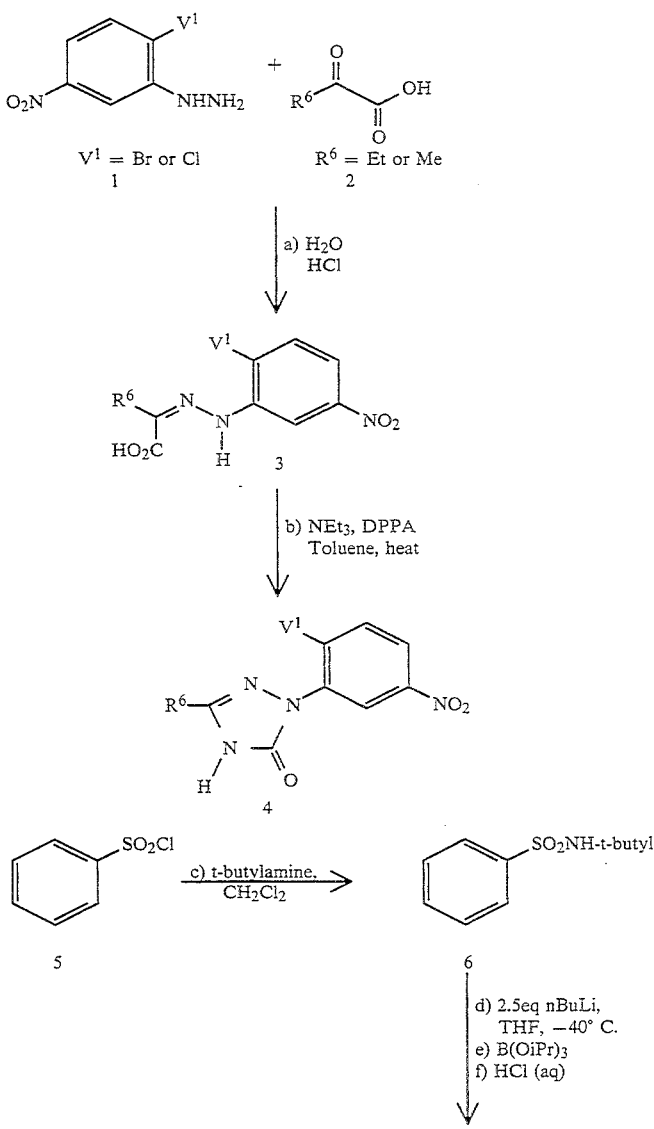

SCHEME 1

-continued
SCHEME 1
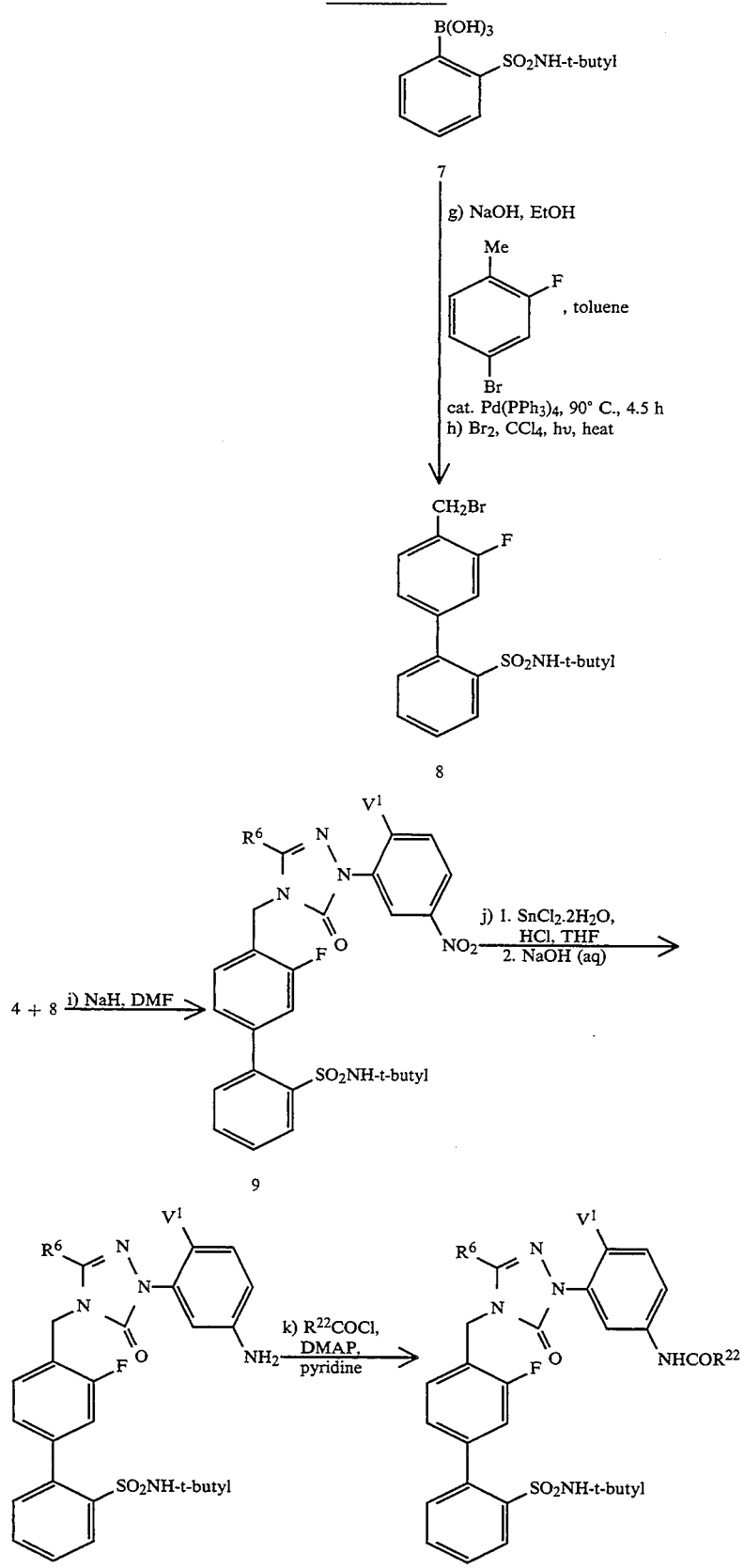

SCHEME 1

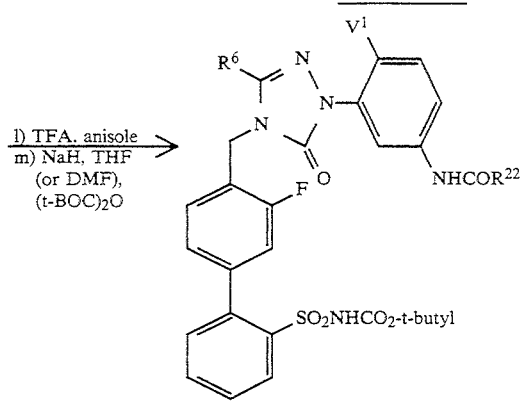

The synthesis of compounds of formula (I) wherein $V^1$ is $CF_3$ and $V^2$ is $NHCOR^{22}$ is presented in Scheme 2. Intermediate 9a (9, where $V^1$ is Br), based on literature conditions [D.-B. Su, J.-X. Duan, and Q.-Y. Chen, *Tetrahedron Lett.*, 32, 7689 (1991)], is heated at about 120° C. with methyl chlorodifluoroacetate, cuprous iodide, potassium fluoride, and potassium bromide in DMF, resulting in displacement of bromo by trifluoromethyl to give 13. The nitro group is hydrogenated in the presence of platinum oxide in a mixture of ethanol and ethyl acetate to give the amine 14. By the methods of Scheme 1, 14 is transformed to the target compound 15.

SCHEME 2

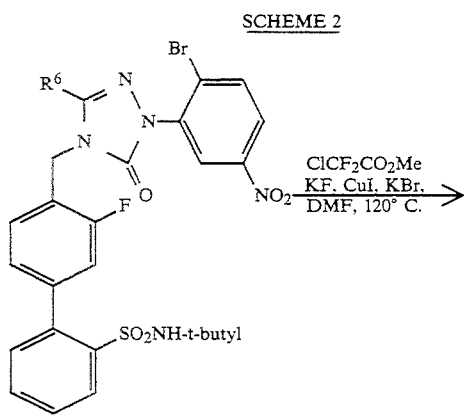

9a  $R^6$ = Et or Me

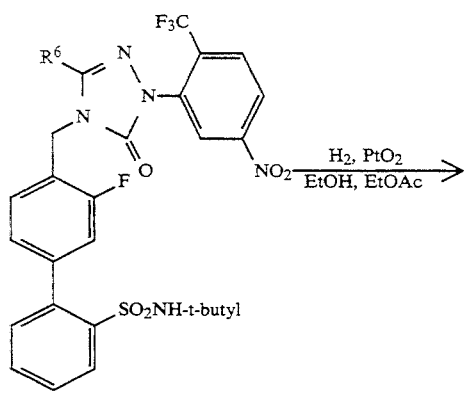

13

-continued
SCHEME 2

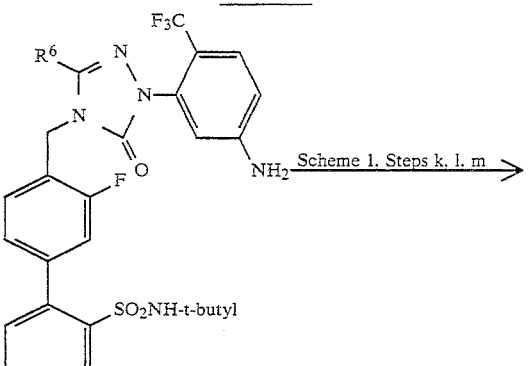

14

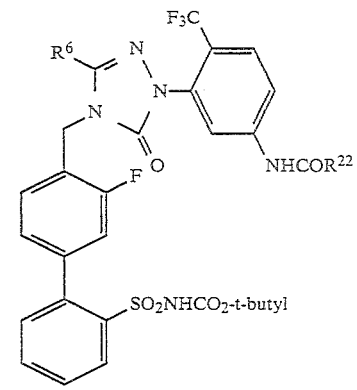

A route to compounds of formula (I) wherein $V^1$ is Br or Cl and $V^2$ is $CONHR^{22}$ is outlined in Scheme 3. The 4-halobenzoic acid ethyl ester 16 is treated with concentrated nitric acid at 0° C., resulting in nitration at the 3-position. The nitro group is reduced to the amine with stannous chloride in the presence of concentrated hydrochloric acid. The resulting amine is diazotized (sodium nitrite, aqueous HCl) and then reduced (stannous chloride, concentrated HCl) according to the method of H. Stroh and G. Westphal, *Chem. Ber.*, 96, 184 (1963). The resulting arylhydrazine hydrochloride 17 is condensed with the α-keto acid and then reacted with diphenylphosphoryl azide as in Scheme 1 to yield the triazolinone 18, which is alkylated with 8 as in Scheme 1 to give 19. Heating 19 with an aliphatic amine $R^{22}NH_2$ affords the amide product 20. This is elaborated to the target compound 21 by the methods of Scheme 1.

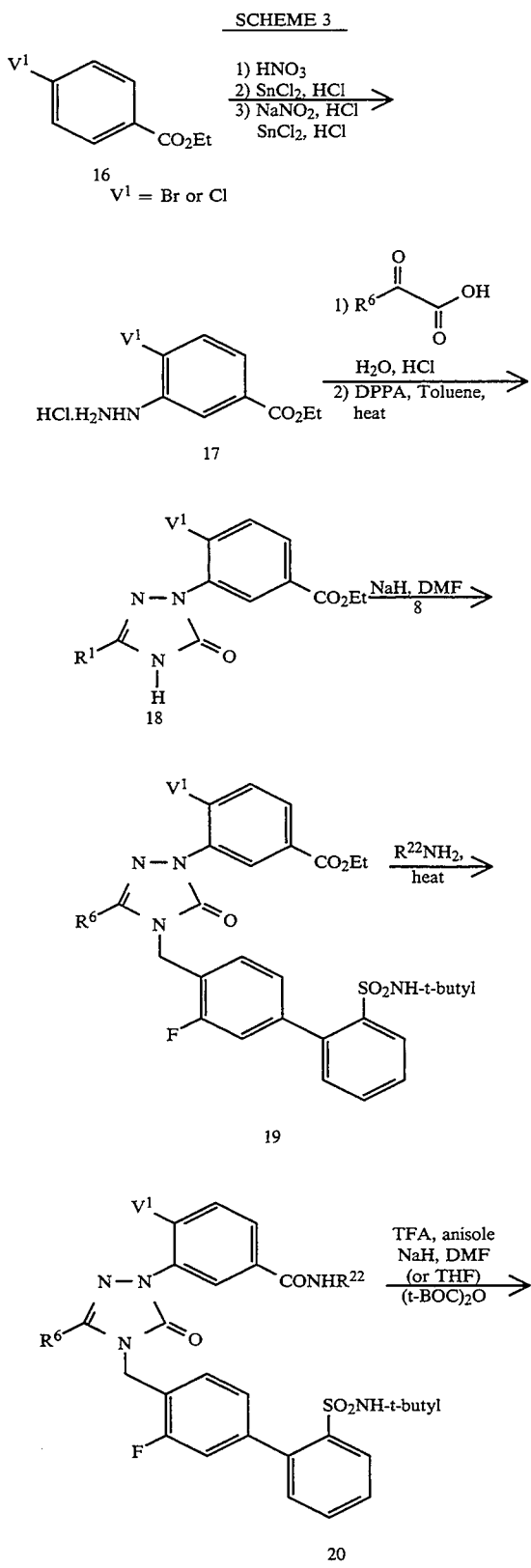

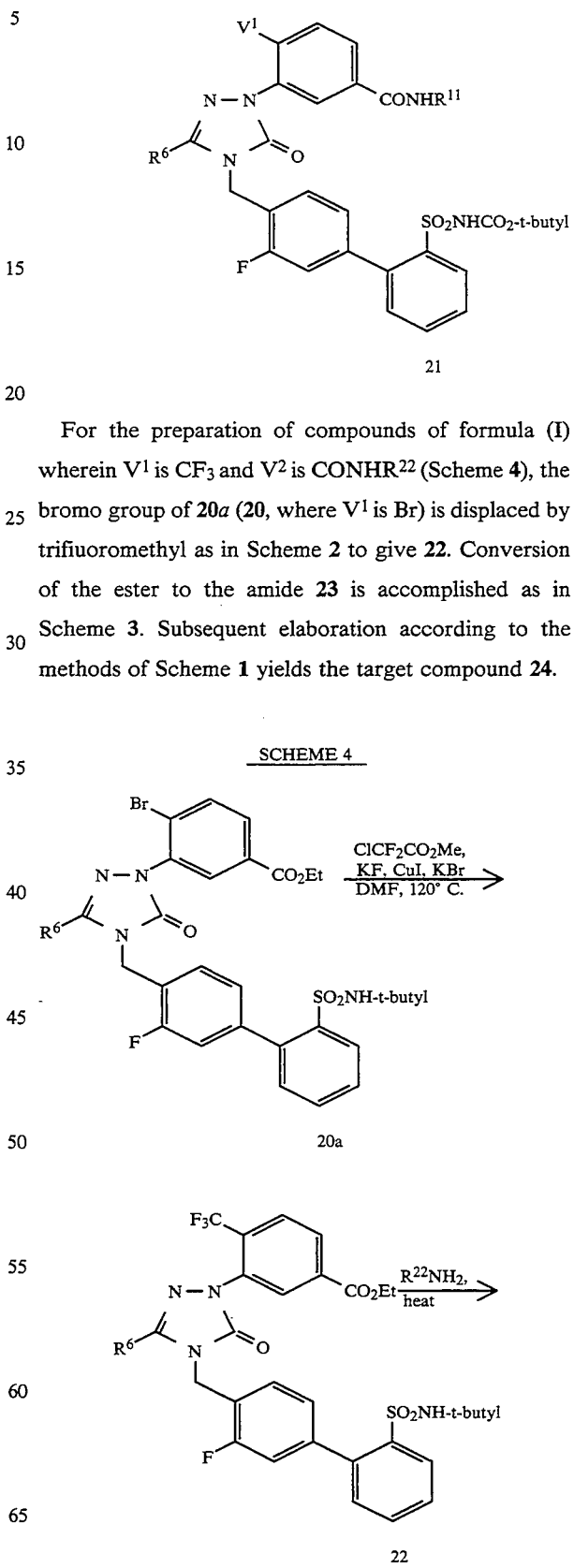

For the preparation of compounds of formula (I) wherein $V^1$ is $CF_3$ and $V^2$ is $CONHR^{22}$ (Scheme 4), the bromo group of 20a (20, where $V^1$ is Br) is displaced by trifluoromethyl as in Scheme 2 to give 22. Conversion of the ester to the amide 23 is accomplished as in Scheme 3. Subsequent elaboration according to the methods of Scheme 1 yields the target compound 24.

-continued
SCHEME 4

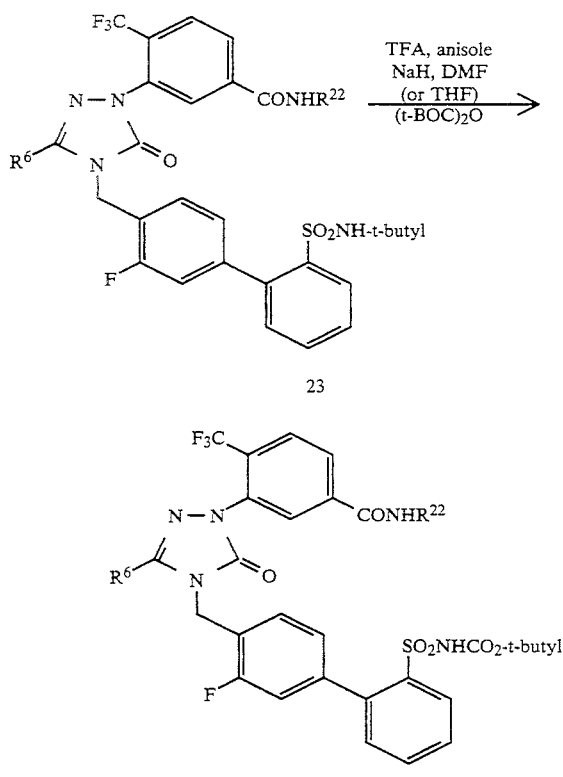

It will be recognized by those skilled in the art that other reagents may be substituted for those shown above providing they are compatible with the structures shown. In addition, the order of steps in some of these reaction sequences may be varied. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts. with organic and inorganic acids may be prepared; e.g., HCl, HBr, $H_2SO_4$, $H_3PO_4$, methanesulfonic, toluene-sulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) are suspended in 5 mM Tris-0.25M Sucrose, pH 7.4 buffer (50 ml) homogenized, and then centrifuged. The mixture is filtered through a cheesecloth and the supernatant is centrifuged for 30 minutes at 20,000 rpm at 4° C. The pellet thus obtained is resuspended in 30 ml of 50 mM Tris-5 mM $MgCl_2$ buffer containing 0.2 mg/ml Bacitracin and the suspension is used for 100 assay tubes. Samples tested for screening are done in duplicate. To the membrane preparation (0.25 ml) there is added $^{125}$I-Sar$^1$Ile$^8$-angiotensin II [obtained from New England Nuclear] (10 gl; 20,000 cpm) with or without the test sample and the mixture is incubated at 37° C. for 90 minutes. The mixture is then diluted with ice-cold 50 mM Tris-0.9% NaCl, pH 7.4 (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration (IC$_{50}$) of a potential AII antagonist which gives 50% displacement of the total specifically bound $^{125}$I-Sar$^1$Ile$^8$-angiotensin II is presented as a measure of the efficacy of such compounds as AII antagonists.

Angiotensin Radioligand Receptor Binding Assays Using Rat and Human Adrenal Cortex Preparation The preparation of membranes from various tissues and specific [$^{125}$I]Sar$^1$,Ile$^8$-Angiotensin II binding assays was as described in R. S. L. Chang, et al., *Journal of Pharmacology and Experimental Therapeutics*, 262, pp.133–138 (1992), with the exception that bovine serum albumin (BSA) was omitted in the binding assay buffers for the rat adrenat assay. BSA (2 mg/ml) was added to the binding buffer for the human adrenal assay. Specific [$^{125}$I]Sar$^1$,Ile$^8$-Angiotensin II binding was defined as the difference between total and nonspecific binding; IC$_{50}$ values were determined by regression analysis of displacement curves. Since both AT$_1$ and AT$_2$ receptor subtypes were present in these tissues, the IC$_{50}$ values on AT$_1$ and AT$_2$ were determined in the presence of 1 μM of PD 121981 (WL-19) or Losartan to prevent binding of the radioligand to AT$_2$ and AT$_1$, respectively.

Receptor Assay Using Rat Brain. Membrane Preparation

Membranes from rat brain (thalamus, hypothalamus and midbrain) are prepared by homogenization in 50 mM Tris HCl (pH 7.4), and centrifuged at 50,000×g. The resulting pellets are washed twice in 100 mM NaCl, 5 mM $Na_2$.EDTA, 10 mM $Na_2HPO_4$ (pH 7.4) and 0.1 mM PMSF by resuspension and centrifugation. For binding assays, the pellets are resuspended in 160 volumes of binding assay buffer (100 mM NaCl, 10 mM $Na_2HPO_4$, 5 mM $Na_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For [$^{125}$I]Sar$^1$,Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]-Sar$^1$,Ile$^8$-angiotensin II (23-46 pM) are added to duplicate tubes. The receptor membrane preparation (500 μl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

Using the methodology described above, representative compounds of this invention could be evaluated and an IC$_{50}$<50 μM determined, thereby demonstrating and confirming the utility of the compounds of the invention as effective A II antagonists.

The antihypertensive effects of the compounds described in the present invention may be evaluated using the methodology described below:

Male Charles River Sprague-Dawley rats (300-375 gm) are anesthetized with methohexital (Brevital; 50 mg/kg i.p.) and the trachea is cannulated with PE 205 tubing. A stainless steel pithing rod (1.5 mm thick, 150 mm long) is inserted into the orbit of the fight eye and down the spinal column. The rats are immediately placed on a Harvard Rodent Ventilator (rate—60 strokes per minute, volunto—1.1 cc per 100 grams body weight). The fight carotid artery is ligated, both left and fight vagal nerves are cut, and the left carotid artery is cannulated with PE 50 tubing for drug administration, and body temperature is maintained at 37° C. by a thermostatically controlled heating pad which received input from a rectal temperature probe. Atropine (1 mg/kg i.v.) is then administered, and 15 minutes later propranolol (1 mg/kg i.v.). Thirty minutes later antagonists of formula I are administered intravenously or orally. Angiotensin II is then typically given at 5, 10, 15, 30, 45 and 60 minute intervals and every half-hour thereafter for as long as the test compound showed activity. The change in the mean arterial blood pressure is recorded for each angiotensin II challenge and the precent inhibition of the angiotensin II response is calculated.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, s ointments, inserts, gels, and the. like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules. or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidine sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drag combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15–200 mg) and nifedipine (5–60 mg) plus an angiotensin II antagonist of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carder, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, com starch or gelatin; an excipient such as microcrystalline cellulose; a disintegrating agent such as com starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to mateddais of the above type, a liquid carder such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto. All $^1$H-NMR spectra were recorded on a Varian XL-300 Fourier transform spectrometer. Chemical shifts are reported as (parts per million) downfield from tetramethyl silane. Mass spectra were obtained from the Merck and Co. mass spectral facility in Rahway N.J. Analytical TLC was conducted on E. M. Merck precoated silica plates (0.25 mm in glass, Kieselgel 60 $F_{254}$) with UV visualization. All chromatography was conducted on E. M. Merck silica gel. All reactions were carded out under an atmosphere of dry nitrogen under standard conditions for those skilled in the art.

EXAMPLE 1

2-[2-Bromo-5-(valerylamino)phenyl]-4-[[2'-[N-(t-butoxycarbonyl)sulfamoyl]-3-fluorobiphenyl-4-yl]methyl]-2,4-dihydro-5-ethyl-3H-1,2,4-triazol-3-one Step A: 2-Ketobutyric acid 2-bromo-5-nitrophenylhydrazone To a stirred mixture of 2.00 g (8.62 mmol) of 2-bromo-5-nitrophenylhydrazine [obtained by diazotization of the corresponding amine (Stroh and Westphal, Chem. Ber. 1963, 96, 184)] in 20 mL of water was added 2 mL of concentrated hydrochloric acid and 880 mg (8.62 mmol) of 2-ketobutyric acid (dissolved in 2 mL water). Ten mL of water was added to facilitate stirring, and the mixture was stirred at room temperature for 1 hour when TLC (10% MeOH/$CH_2Cl_2$–0.1% HOAc) indicated disappearance of all starting hydrazine. Ethyl acetate was added, and the layers were separated. The organic layer was washed with water, brine and dried over anhydrous $Na_2SO_4$. Filtration and removal of volatiles afforded 2.66 g of an orange solid (mp 263°–265 ° C.) sufficiently pure to be used directly in the next reaction. Mass spectrum m/e 316, 318 $(M+1)^+$.

400 MHz $^1$H NMR (DMSO-$d_6$)δ1.07(t, J=7.6 Hz, 3 H), 2.58 (m, 2H), 7.62 (m, 1H), 7.86 (m, 1H), 8.15 (m, 1H)

Step B: 2-(2-Bromo-5-nitrophenyl)-2,4-dihydro-5-ethyl-3H-1,2,4-triazol-3-one

To a stirred solution of 2.66 g (8.42 mmol) of 2-ketobutyric acid 2-bromo-5-nitrophenylhydrazone (from Step A) and 1.2 mL (8.42 mmol, 850 mg) of triethylamine in 100 mL of toluene was added 1.81 mL (8.42 mmol, 2.32 g) of diphenylphosphoryl azide. The reaction mixture was heated gradually to 115° C. and stirred for 4 hours when TLC (5% MeOH/$CH_2Cl_2$) indicated complete disappearance of starting material. Solvents were evaporated in vacuo and the residue was taken up in ethyl acetate and washed twice with water and then with brine, and dried ($Na_2SO_4$). The crude product obtained after filtration and removal of solvents was flash chromatographed over silica gel (gradient elution using 0.5–2.0% MeOH in $CH_2Cl_2$) to afford 2.00 g (76%) of a cream-colored solid, mp 191°–193° C., homogeneous by TLC (5% MeOH/$CH_2Cl_2$). Mass spectrum (FAB) m/e 312, 314 $(M+H)^+$.

400 MHz $^1$H NMR (CDCl$_3$)δ1.29(t, J=7.6 Hz, 3H), 2.63 (q, J=7.6 Hz, 2H), 7.89(d, J=8.9Hz, 1H), 8.13(dd, J=2.7, 8.9 Hz, 1H), 8.34 (d, J=2.7 Hz, 1H), 11.5 (s, br, 1H)

Step C: N-t-Butyl-benzenesulfonamide

To a solution of benzenesulfonyl chloride in anhydrous $CH_2Cl_2$ (0.5M solution) cooled to 0° C. under $N_2$ was added t-butylamine (2.2 equiv) slowly through a dropping funnel. After completion of addition, the reaction was stirred at toom temperature for 12 hours. The solvent was removed under reduced pressure, and the residue was extracted into ether and washed with 2N NaOH, $H_2O$ and brine. The organic phase was dried over anhydrous $MgSO_4$ and concentrated in vacuo to afford the titled product, which was used directly in the next step.

Step D: 2-(N-t-Butylsulfamoyl)phenylboronic acid

To a solution of 11.2 mmol of N-t-butylbenzenesulfonamide (from Step C) in anhydrous THF (20 mL) cooled to −40° C. under $N_2$ was addeel 2.5M n-BuLi solution (11.2 mL, 2.5 equiv). The mixture was warmed to room temperature and stirred for 2 hours. To the mixture, containng the dianion at 0° C., was added triisopropyl borate (3.9 mL, 1.5 equiv). The next day, 2 N HCl (3 mL) was added and the mixture was stirred for 1 hour. The solvent was removed under reduced pressure and the residue was extracted with EtOAc. The organic solution was washed with 2N HCl, $H_2O$ and brine. The organic phase was dried over anhydrous MgSO$_4$ and concentrated in vacuo to afford the titled compound. The material was used in the next step without further purification.

Step E: N-t-Butyl-3'-fluoro-4'-methyl-2-biphenylsulfonamide

To a vigorously stirred solution of 4.27 g (16.6 mmol) of 2-(N-t-butylsulfamoyl)phenylboronic acid (from Step D), 32 mmol (26 mL of a 1.25N aqueous solution) of NaOH in 40 mL of ethanol was added 1.89 g (10 mmol, 1.27 mL) of 4-bromo-2-fluorotoluene, 60 mL of toluene, and 289 mg (0.25 mmol) of tetrakis(tfiphenylphosphine)palladium. The mixture was stirred at 90° C. for 4.5 h, cooled to room temperature, and the volatiles were removed in vacuo. The residue was extracted with ethyl acetate (3×) and the combined organic layers were washed with water, brine, and dried (Na$_2$SO$_4$). The crude product obtained after filtration and removal of solvents was flash chromatographed over silica gel (elution with hexane-EtOAc) to afford 2.96 g (92%) of the desired product cleanly (TLC in 4:1 hexane-EtOAc) as an off-white foam; mass spectrum (FAB) m/e 322 (M+1)+.

400 MHz $^1$H NMR (CDCl$_3$)δ1.01 (s, 9H), 2,32 (s, 3H), 3.59(br s, 1H), 7.13–7.28 (m, 4H), 7.44–7.56 (m, 2H), 8.14 (dd, J=7.8, 1.4 Hz, 1H).

Step F: 4'-(Bromomethyl)-N-t-butyl-3'-fluoro-2-biphenylsulfonamide

A solution of 1.08 g (3.36 mmol) of N-t-butyl-3'-fiuoro-4'-methyl-2-biphenylsulfonamide (from Step E) in 20 in mL of CCl$_4$ was stirred at reflux under irradiation from a 100-watt tungsten lamp as a solution of 3.5 mmol of bromine in approximately 13 mL of CCl$_4$ was added dropwise over 1.5 hour. After being stirred at reflux overnight, the solution was cooled and concentrated. The residue was crystallized from EtOAc-hexane to give 1.10 g of the title compound as an off-white solid, mp 138°–140° C. (estimated purity 87%, containing minor unbrominated and dibrominated contaminants by TLC); mass spectrum (FAB) m/e 400, 402 (M+1)+.

400 MHz $^1$H NMR (CDCl$_3$)δ1.01(s, 9H), 3.56 (br s, 1H), 4.54(s, 2H), 7.2–7.6 (m, 6H), 8.15 (dd, J=8, 1.3 Hz, 1H).

Step G: 2-(2-Bromo-5-nitrophenyl)-4-[[2'-(N-t-butylsulfamoyl)-3-fluorobiphenyl-4-yl]methyl]-2,4-dihydro-5-ethyl-3H-1,2,4-triazol-3-one A mixture of 2.00 g (6.39 mmol) of 2-(2-bromo-5-nitrophenyl)-2,4-dihydro -5-ethyl-3H-1,2,4-triazol-3-one (from Step B) and 184 mg (7.67 mmol) of sodium hydride in 7 mL of DMF was stirred at 50° C. for 3 hours. A solution of 4'-(bromomethyl)-N-t-butyl-3'-fluoro -2-biphenylsulfonamide (from Step F dissolved in 6 ml of DMF was then added and the resulting mixture was stirred at 50° C. for another 3 hours. The reaction mixture was quenched by addition of water followed by extractions with EtOAc, CH$_2$Cl$_2$, and MeOH. Water was removed and the organic layers were washed with brine, and dried over anhydrous Na$_2$SO$_4$. The entire crude product mixture thus obtained was flash chromatographed over silica gel (gradient elution using 0.5–2.0% MeOH in CH$_2$Cl$_2$) to afford 3.54 g (88%) of the title compound as a yellow solid (contaminated with some upper and lower Rf impurities by TLC but suitable for use in the next step without further purification), mp 223°–225° C.; mass spectrum (FAB) m/e 631, 633 (M+1)+.

400 MHz $^1$H NMR (CDCl$_3$) δ0.87 (s, 9H), 1.15 (t, J=7.4 Hz, 3 H), 2.49 (q, J=7.4 Hz, 2H), 4.86 (s, 2H), 7.08–7.18 (m, 3H), 7.19–7.26 (m, 1H), 7.33–7.45 (m, 2H), 7.77 (d, J=8.8 Hz, 1 H), 7.92–8.05 (m, 2H), 8.10 (d, J=2.7 Hz, 1H).

Step H; 2-(5-Amino-2-bromophenyl)-4-[[2'-(N-t-butylsulfamoyl) -3-fluorobiphenyl-4-yl]methyl]-2,4-dihydro-5-ethyl-3H -1,2,4-triazo-3-one At 0° C., to a stirred solution of 1.00 g (1.58 mmol) of 2-(2-bromo-5-nitrophenyl)-4-[[2'-(N-t-butylsulfamoyl)-3-fluorobiphenyl-4-yl]methyl]-2,4-dihydro-5-ethyl-3H-1,2,4-triazol-3-one (from Step G) in 15 mL of anhydrous THF was added dropwise a solution of 2.50 g (11.1 mmol) of stannous chloride dihydrate in 15 mL of concentrated HCl. After stirring at room temperature for 6 hours, the reaction mixture was treated with 50% aqueous NaOH, ice, and extracted with EtOAc twice. The organic layers were combined and washed with water, brine and dried over anhydrous Na$_2$SO$_4$. The crude product obtained after filtration and removal of volatiles was flash chromatographed over silica gel (gradient elution using 0.5–3.0% MeOH in CH$_2$Cl$_2$) to afford (in addition to 481 mg of recovered starting material) 213 mg of the desired product (with very slight impurities by TLC), mp 108°–110° C.; mass spectrum (FAB) m/e 601,603 (M+1)+and 546, 548 (M-t-Bu)+.

400 MHz $^1$H NMR (CDCl$_3$)δ1.03 (s, 9H), 1.28 (t, J=7.4 Hz, 3 H), 2.57 (q, J=7.4 Hz, 2H), 3.61 (s, 1H), 3.78 (s, 2H), 5.28 (s, 2H), 6.59 (dd, J=2.8, 8.7 Hz, 1H), 6.78(d, J=2.8 Hz), 7.20–7.60 (m, 7H), 8.14 (d, J=7.6 Hz, 1H).

Step I: 2-[2-Bromo-5-(valerylamino)phenyl]-4-[[2'-(N-t -butylsulfamoyl)-3-fluorobiphenyl-4-yl]methyl]-2,4-dihydro-5-ethyl-3H 1,2,4-triazo-3-one To a mixture of 71 mg (0.12 mmol) of 2-(5-amino-2-bromophenyl)-4-[[2'-(N-t-butylsulfamoyl)-3-fluorobiphenyl-4-yl]methyl]-2,4-dihydro-5-ethyl-3H-1,2,4-triazol-3-one (from Step H), and 14 mg (0.12 mmol) of 4-(N,N-dimethyl)aminnopyridine (DMAP) in 1 mL of dry pyridine was added 71 mg (0.59 mmol) of valeryl chloride, and the resulting mixture was stirred overnight at room temperature. The reaction was quenched by addition of water, and the organic material was extracted by ethyl acetate twice. The combined organic layers were washed twice with water, brine, and dried over anhydrous Na$_2$SO$_4$. The crude product obtained after filtration and evaporation of volatiles was flash chromatographed over silica gel (gradient elution using 0.5–2.0% MeOH in CH$_2$Cl$_2$) to afford 36 mg (44%) of the title compound as a white solid, mp 249°–251° C., homogeneous by TLC; mass spectrum (FAB) m/e 687 (M+1)+.

400 MHz $^1$H NMR (CDCl$_3$)δ0.90 (t, J=7.4 Hz, 3 H), 1.02 (s, 9H), 1.27 (t, J=7.4 Hz, 3H), 1.35 (m, 2H), 1.65 (m, 2H), 2.32 (q, J=7.7 Hz, 2H), 2.57 (q, J=7.4 Hz, 2H), 3.68 (s, 1H), 5.00 (s, 2H), 7.20–7.35 (m, 3H), 7.40–7.60 (m, 5H), 7.70 (d, J=2.3 Hz, 1H), 8.15 (dd, J=1.0, 7.7 Hz, 1H).

Step J: 2-[2-Bromo-5-(valerylamino )phenyl]-2,4-dihydro-5-ethyl -4-[(3-fluoro-2'-sulfamoylbiphenyl-4-yl)methyl]-3H-1,2,4-triazol-3-one A solution of 33 mg (0.048 mmol) of 2-[2-bromo-5(valerylamino)phenyl]-2,4-[[2'-(N-t-butylsulfamoyl)-3-fluorobiphenyl-4-yl methyl]-2,4-dihydro-5-ethyl-3H-1,2,4-triazol-3-one (from Step I), 2 drops of anisole, and 0.5 mL of anhydrous trifluoroacetic acid (TFA) was stirred at room temperature overnight. The residual TFA was removed by a stream of nitrogen and the residue was flash chromatographed over silica gel (gradient elution using 0.5–2.0% MeOH in CH$_2$Cl$_2$) to afford 24 mg (80%) of the desired product (containing very minor lower Rf impurities), mp 223°–225° C.; mass spectrum (FAB) m/e 629, 631 (M+1)+.

400 MHz $^1$H NMR (CD$_3$OD)δ0.95 (t, J=7.4 Hz, 3 H), 1.25 (t, J=7.5 Hz, 3 H), 1.40 (m, 2H), 1.68 (m, 2H), 2.37 (m, 2H), 2.65 (q, J=7.5 Hz, 2H), 5.08 (s, 2H), 7.20–7.38 (m, 4H), 7.55–7.70 (m, 4H), 7.90 (d, J =2.5 Hz, 1H), 8.10 (dd, J=1.4, 7.9 Hz, 1H).

Step K: 2-[2-Bromo-5-(valerylamino)phenyl]-4-[[2'-[N-(t-butoxycarbonyl)sulfamoyl]-3-fluorobipheny 1-4-yl]methyl]2,4-dihydro-5-ethyl-3H-1,2,4-triazol-3-one A mixture of 24 mg (0.038 mmol) of 2-[2-bromo-5(valerylamino)phenyl]-2,4-dihydro-5-ethyl-4-[(3-fluoro-2'-sulfamoylbiphenyl-4-yl)methyl]-3H-1,2,4-triazol-3-one (from Step J), and 1.1 mg (0.046 mmol of sodium hydride in 0.5 mL of DMF was stirred at 50° C. for 4 hours. Subsequently, 17 mg (0.076 mmol) of di-t-butyl dicarbonate was added and the reaction mixture was stirred at 55° C. overnight. Volatiles were evaporated in vacuo and the residue was taken up in CH$_2$Cl$_2$ and washed with water at pH 2 (acidified with 2N HCl), brine, and dried over anhydrous Na$_2$SO$_4$. The crude material obtained after filtration and evaporation of solvents was flash chromatographed over silica gel (gradient elution using 0.5–2.0% MeOH in CH$_2$Cl$_2$) to give 12 mg of desired material as a white, glassy solid, mp 125°–127° C., homogeneous by TLC; mass spectrum (FAB) m/e 731 (M+1)+.

400 MHz $^1$H NMR (CD$_3$OD) δ0.95 (t, J=7.3 Hz, 3 H), 1.26 (m, 3 H), 1.30 (s, 9H), 1.40 (m, 2H), 1.65 (m, 2H), 2.38 (m, 2H), 2.66 (m, 2H), 5.10 (s, 2H), 7.15–7.40 (m, 4H), 7.55–7.75 (m, 4H), 7.93 (d, J=2.5 Hz, 1H), 8.17 (dd, J=1.3, 8.0 Hz, 1H).

EXAMPLE 2

4-[[2'-[N-(t-Butoxycarbonyl)sulfamoyl]-3-fluorobiphenyl-4-yl]methyl]-2,4-dihydro-5-ethyl-2-[2-(trifluoromethyl)-5-(valerylamino)phenyl]3 H-1,2,4-triazo1-3-one Step A: 4-[[2'-(N-t-Butylsulfamoyl)-3-fluorobiphenyl-4-yl]methyl]2,4-dihydro-5-ethyl-2-[5-nitro-2-(trifluoromethyl)phenyl]is 3H-1,2,4-triazol-3-one.

A mixture of 88 mg (1.52 mmol) of potassium fluoride, 226 mg (1.90 mmol) of potassium bromide, 800 mg (1.27 mmol) of 2,-(2-bromo-5-nitrophenyl)-4-[[2'-(N-t-butylsulfamoyl)-3-fluorobiphenyl -4-yl]methyl]-2,4-dihydro-5-ethyl-3H-1,2,4-triazol-3-one (from Example 1, Step G) and 2 mL of DMF was stirred at 120° C. in a sealed tube. Subsequently, 267 μL (2.53 mmol, 366 mg) of methyl 2-chloro-2,2-difluoroacetate was added and the mixture stirred overnight at 120° C. The reaction mixture was quenched by the addition of water, 5% citric acid and the organic material was extracted with EtOAc 3 times. The combined organic layers were washed with water and brine and dried over anhydrous Na$_2$SO$_4$. The crude material obtained after filtration and evaporation of volatiles was flashed chromatographed over silica gel (gradient elution using 5:1 to 2:1 hexane/EtOAc) to give 388 mg (49%) of the desired product as a yellow solid (containing a slight amount of a higher Rf impurity by TLC), mp 167°–169° C. mass spectrum (FAB) m/e 622 (M+1)+.

400 MHz $^1$H NMR (CDCl$_3$) δ1.02 (s, 9H), 1.29 (t, J=7.4 Hz, 3 H), 2.60 (q, J=7.4 Hz, 2H), 3.59 (s, 1H), 5.00 (s, 2H), 7.20–7.60 (m, 6H), 7.99 (d, J=8.7 Hz, 1H), 8.15 (dd, J=1.4, 8.8 Hz, 1 H), 8.35 (dd, J=1.5, 8.7 Hz, 1H), 8.46 (d, J=2.3 Hz, 1H).

Step B: 2-[5-Amino-2-(trifluoromethyl)phenyl]-4-[[2'-(N-t-butylsulfamoyl)-3-fluorobiphenyl-4-yl]methyl]-2,4-dihydro-5-ethyl-3H-1,2,4-triazol-3-one.

A mixture of 388 mg (0.625 mmol) of 4-[[2'-(N-t-butylsulfamoyl)-3-fluorobiphenyl-4-yl]methyl]-2,4-dihydro-5-ethyl-2-[5-nitro-2-(trifluoromethyl)phenyl]-3H-1,2,4-triazol-3-one (from Step A), 6 mL of EtOH, 8 mL of EtOAc, and 30 mg of 5% PtO$_2$ was shaken with hydrogen for 3.5 hours on a Parr hydrogenation apparatus. Removal of the catalyst followed by evaporation of volatiles gave 383 mg (quantitative) of a cream-colored solid [top >105° C. (gradual)] of sufficient purity to be used in the next step without further purification; mass spectrum (FAB) m/e 599 (M+Li)+.

400 MHz $^1$H NMR (CDCl$_3$)δ1.01 (s, 9H), 1.26 (t, J=7.5 Hz, 3 H), 2.55 (q, J=7.5 Hz, 2H), 3.60 (s, 1H), 4.13 (br s, 2 H), 4.98 (s, 2H), 7.20–7.40 (m, 6H), 7.58–7.60 (m, 3H), 8.15 (dd, J=1.4, 7.8 Hz, 1 H)

Step C: 4-[[2'-(N-t-Butylsulfamoyl)-3-fluorobiphenyl-4-yl]methyl]-2,4-dihydro-5-ethyl-2-[2-(trifluoromethyl)-5-(valerylarnino)phenyl]-3H-1,2,4-triazol-3-one The acylation of 2-[5-amino-2-(trifluoromethyl)-phenyl]-4-[[2'-(N-t-butylsulfamoyl)-3-fluorobiphenyl-4-yl]methyl]-2,4-dihydro-5-ethyl-3H-1,2,4-triazol-3-one (from Step B) was carried out as described for Example 1, Step I. The crude material obtained was of sufficient purity to be used in the next step without further purification, mp 243°–245° C.; mass spectrum (FAB) m/e 676 (M+H)+.

400 MHz $^1$H NMR (CDCl$_3$)δ0.92 (t, J=7.4 Hz, 3H), 1.01 (s, 9H), 1.25 (t, J=7.5 Hz, 3 H), 1.35 (m, 2H), 1.63 (m, 2H), 2.34 (m, 2H), 2.55 (q, J=7.4 Hz, 2H), 3.72 (s, 1H), 4.99 (s, 2H), 7.20–7.40 (m, 3H), 7.55–7.90 (m, 6H), 8.15 (dd, J=1.4, 7.8 Hz, 1H)

Step D: 2,4-Dihydro-5-ethyl-4-[(3-fluoro-2'-sulfamoyl-biphenyl-4-yl) methyl]-2-[2-(trifluoromethyl)-5-(valerylamino)phenyl]3H-1,2,4-triazol-3-one The removal of the t-butyl group of 4-[[2'-(N-t-butylsulfamoyl)-3-fluorobiphenyl-4-yl]methyl]-2,4-dihydro-5-ethyl-2[2-(trifluoromethyl)-5-(valerylamino)phenyl]-3H-1,2,4-triazo 1,3-one (from Step C) was carded out as described for Example 1, Step J. The crude material obtained was flash chromatographed over silica gel (gradient elution using 0.5–4.0% MeOH in CH$_2$Cl$_2$) to give 100 mg (64% over two steps) of the desired compound as a cream-colored solid, mp 192°–194° C.; mass spectrum (FAB) m/e 620 (M+H)+.

400 MHz $^1$H NMR (CDCl$_3$) δ0.89 (t, J=7.4 Hz, 3H), 1.26 (t, J=7.4 Hz, 3H), 1.37 (m, 2H), 1.63 (m, 2H), 2.30 (m, 2H), 2.58 (q, J=7.4 Hz, 2H), 4.51 (s, 2H), 4.97 (s, 2H), 7.20–7.35 (m, 3H), 7.48–7.75 (m, 5H), 8.14 (dd, J=1.4, 7.9 Hz, 1 H)

Step E: 4-[[2'-[N-(t-Butoxycarbonyl)sulfamoyl]-3-fluorobiphenyl -4-yl]methyl]-2,4-dihydro-5-ethyl-2-[2-(trifluoromethyl)-5-(valerylamino)phenyl]-3H-1,2,4-triazol-3-one This reaction was carded out essentially the same way as that described for Example 1, Step K, except that 2,4-dihydro-5-ethyl -4-[(3-fluoro-2'-sulfamoyl-biphenyl-4-yl)methyl]-2-[2-(trifluoromethyl) -5-(valerylamino)phenyl]-3H-1,2,4-triazol-3-one (from Step D) was used as the starting material. The crude material obtained was flash chromatographed over silica gel (gradient elution using 0.5–4.0% MeOH in CH$_2$Cl$_2$) to give a 39% yield of the desired compound as a cream-colored solid, mp 121°–123° C.; mass spectrum (FAB) m/e 742 (M+H)+.

Analysis (C$_{34}$H$_{37}$F$_4$N$_5$O$_6$S) Calcd: C, 56.74; H, 5.18; N, 9.73. Found: C, 56.52; H, 5.13; N, 9.58.

400 MHz $^1$H NMR (CD$_3$OD) δ0.95 (t, J=7.3 Hz, 3H), 1.26 (t, J=7.4 Hz, 3H), 1.30 (s, 9H), 1.407 (m, 2H), 1.66

(m, 2H), 2.41 (m, 2H), 2.68 (q, J=7.4 Hz, 2H), 5.09 (s, 2H), 7.10–7.40 (m, 4H), 7.55–7.85 (m, 4H), 7.96 (s, 1 H), 8.16 (dd, J=1.3, 8.0 Hz, 1 H)

EXAMPLE 3

4- [[2'-[N-(t-Butoxycarbonyl)sulfamoyl]-3-fluorobiphenyl-4-yl]methyl]-2-[5-(N-n-butylcarbamoyl)-2-(trifluoromethyl)phenyl]-2,4-dihydro-5-ethyl-3H-1,2,4-triazol-3-one Step A: Ethyl 4-Bromo-3-nitrobenzoate At 0° C., to a stirred solution comaining 35 mL of concentrated nitric acid was added 3.5 g (15.3 mmol) of ethyl 4-bromobenzoate. After 30 min at 0° C., the reaction mixture was treated with ice and ethyl acetate was added. The phases were separated, and the organic phase was treated with 5% NaHCO3, water, and brine, and dried over anhydrous Na2SO4. Evaporation of volatiles gave 3.68 g (88%) of a white solid, homogeneous by TLC (4/1 hexane/EtOAc); mass spectrum (EI) m/e 273, 275 (M+).

200 MHz 1H NMR (CDCl3) δ1.41 (t,J=7.2 Hz, 3 H), 4.42 (q, J=7.2 Hz, 2 H), 7.83 (d, J=8.3 Hz, 1 H), 8.07 (dd, J=1.9, 8.3 Hz, 2H), 8.44 (dd, J=1.9 Hz, 1 H)

Step B: Ethyl 3-Amino-4-bromobenzoate

Ethyl 4-bromo-3-nitrobenzoate was reduced according to the procedure of Example I, Step H, to give the title compound in quantitative yield, homogeneous by TLC (4/1 hexane/EtOAc); mass spectrum (EI) m/e 243,245 (M+).

200 MHz 1H NMR (CD3OD) δ1.35 (t, J=7.2 Hz, 3 H), 4.30 (q, J=7.2 Hz, 2 H), 7.14 (dd, J=2.0, 8.3 Hz, 1 H), 7.44 (m, 2H)

Step C: 4-[[2'-(N-t-Butylsulfamoyl)-3-fluorobiphenyl-4-yl]methyl]-2-[5-carbethoxy-2-(trifluoromethyl)-phenyl]-2,4-dihydro-5-ethyl-3H-1,2,4-triazo-3-one The elaboration of ethyl 3-amino-4-bromobenzoate (from Step B) to the titled compound was achieved via a sequence of transformations analogous to those described for Example 1, Steps A, B, G, and Example 2, Step A. After chromatographic purification, the titled compound was obtained in 25% yield; mass spectrum (FAB) m/e 649 (M+1)+.

400 MHz 1H NMR (CDCl3) δ1.01 (s, 9H), 1.27 (t, J=7.4 Hz, 3H), 1.38 (t, =7.1 Hz, 3 H), 2.57 (q, J=7.4 Hz, 2H), 4.39 (q, J=7.1 Hz, 2 H), 4.99 (s, 2H), 7.23–7.45 (m, 3H), 7.45–7.60 (m, 3 H), 7.85 (d, J=8.4 Hz, 1 H), 8.13–8.20 (m, 3 H)

Step D: 2-[(5-N-n-Butylcarbamoyl-2-trifluoromethyl)-phenyl]-4-[[2'-(N-t-butylsulfamoyl)-3-fluorobiphenyl-4-yl]methyl]-2,4-dihydro-5-ethyl-3H-1,2,4-triazol-3-one 28 mg (0.046 mmol) of 4-[[2'-(N-t-butylsulfamoyl)-3-fluorobiphenyl-4-yl]methyl]-2-[5-carbethoxy-2-(trifluoromethyl)phenyl]-2,4-dihydro-5-ethyl-3H-1,2,4-triazol-3-one (from Step C) was dissolved in 0.75 mL of n-butylamine and heated at 120° C. for 16 hours in a sealed tube. Volatiles were removed under reduced presure and the crude product was flash chromatographed to give 17 mg (59%) of the title compound cleanly (TLC in 19:1 CH2Cl2/MeOH); mass spectrum (FAB) m/e 482 (M+Li)+.

400 MHz 1H NMR (CDCl3) δ0.93 (t, J=7.3 Hz, 3H), 1.02 (s, 9H), 1.27 (t, J=7.4 Hz, 3H), 1.40 (m, 2H), 1.60 (m, 2H), 2.58 (q, J=7.4 Hz, 2H), 3.64 (s, 1H), 4.99 (s, 2H), 6.42 (br s, 1H), 7.23–7.40 (m, 4H), 7.45–7.60 (m, 2 H), 7.85 (m, 3H), 8.14 (dd, J=1.3, 7.8 Hz, 1 H)

Step E: 4-[[2'-[N-(t-Butoxycarbonyl)sulfamoyl]-3-fluorobiphenyl -4-yl]methyl]-2-[5-(N-n-butylcarbamoyl)-2-(trifluoromethyl) phenyl]-2,4-dihydro-5-ethyl-3H-1,2,4-triazol-3-one The elaboration of 2-[(5-N-n-butylcarbamoyl-2-trifluoromethyl)phenyl]-4-[[2'-(N-t-butylsulfamoyl)-3-fluorobiphenyl -4-yl]methyl]-2,4-dihydro-5-ethyl-3H-1,2,4-triazol-3-one (from Step D) to the titled compound was achieved according to procedures analogous to those described for Example 1, Steps J and K. After chromatographic purification, the titled compound was obtained in 57% yield, mp 114°–116° C.; mass spectrum (FAB) m/e 720 (M+1)+.

400 MHz 1H NMR (CD3OD) δ0.97 (t, J=7.3 Hz, 3H), 1.27 (t, J=7.4 Hz, 3H), 1.30 (s, 9H), 1.43 (m, 2H), 1.62 (m, 2H), 2.68 (q, J=7.4 Hz, 2H), 3.40 (m, 2H), 5.10 (s, 2H), 7.15–7.23(m, 2H), 7.28 (t, J=7.8 Hz, 1H), 7.34(dd, J=1.3, 6.3 Hz, 1H), 7.60 (dd, J=1.3, 7.9 Hz, 1H), 7.67(dd, J=1.3, 7.3 Hz, 1H), 7.98–8.09(m, 2 H), 8.10 (m, 1H), 8.15 (dd, J=1.3, 6.8 Hz, 1H)

EXAMPLE 4

2-[2- Bromo-5-(N-n-butylcarbamoyl)phenyl]-4-[[2'-[N-(t-butoxycarbonyl)sulfamoyl]-3-fluorobiphenyl-4-yl]methyl]-2,4-dihydro -5-ethyl-3H-1,2,4-triazol-3-one The elaboration of ethyl 3-amino-4-bromobenzoate (from Example 3, Step B) to the titled compound was achieved via a sequence of transformations analogous to those described for Example 1, Steps A, B, G, and Example 3, Steps D and E. After chromatographic purification, the titled compound was obtained in 49% yield; mass spectrum (FAB) rn/e 738 (M+Li)+.

400 MHz 1H NMR (CD3OD) δ0.96 (t, J=7.3 Hz, 3H), 1.29 (t, J=7.4 Hz, 3H), 1.30 (s, 9H), 1.41 (m, 2H), 1.60 (m, 2H), 2.68 (q, J=7.4 Hz, 2H), 3.37 (t, J=7.1 Hz, 2H), 5.11 (s, 2H), 7.16–7.20(m, 2H), 7.32–7.36 (m, 2H), 7.59–7.61(m, 1H), 7.68 (m, 1H), 7.82–7.96 (m, 3 H), 8.16 (dd, J=1.3, 7.9 Hz, 1H)

EXAMPLE 5

2-[5-(Benzoylamino)-2-bromophenyl]-4-[[2'-[N-(t-butoxycarbonyl)sulfamoyl]-3-fluorobiphenyl-4-yl]methyl]-2,4-dihydro-5-ethyl-3H -1,2,4-triazol-3-one The elaboration of 2-(5-amino-2-bromophenyl)-4-[[2'-(N-t -butylsulfamoyl)-3-fluorobiphenyl-4-yl]methyl]-2,4-dihydro-5-ethyl-3H -1,2,4-triazol-3-one (from Example 1, Step H) to the titled compound was achieved via a sequence of transformations analogous to those described for Example 1 Steps I, J, and K, except that benzoyl chloride was used instead of valeryl chloride in the first step. After chromatographic purification, the titled compound was obtained in 49% yield, mp 154°–156° C.; mass spectrum (FAB) m/e 762, 764 (M+2Li)+.

400 MHz 1H NMR (CDCl3)δ1.25 (s, 9H), 1.28 (t, J=7.4 Hz, 3H), 2.59 (q, J=7.5 Hz, 2H), 4.97 (s, 2H), 7.05–7.75 (m, 10H), 7.79 (d, J=2.5 Hz, 1H), 7.86 (dd, J=2.1, 7.0 Hz, 2H), 8.22 (dd, J=2.1, 7.9 Hz, 1H), 8.5 (s, 1H)

EXAMPLE 6

2-[2- Bromo-5-(propionylamino)phenyl]-4-[[2'-[N-(t-butoxycarbonyl)sulfamoyl]-3-fluorobiphenyl-4-yl]methyl]-2,4-dihydro-5-ethyl-3H -1,2,4-triazol-3-one The elaboration of 2-(5-amino-2-bromophenyl)-4-[[2'-(N-t-butylsulfamoyl) -3-fluorobiphenyl-4-yl]methyl]-2,4-dihydro-5-ethyl-3H -1,2,4-triazol-3-one (from Example 1, Step H) to the titled compound was achieved via a sequence of transformations analogous to those described for Example 1, Steps I, J, and K, except that propionyl bromide was used instead of valeryl chloride in the first step. After chromatographic purification, the titled compound was obtained in 29% yield, mp 146°–148° C.; mass spectrum (FAB) m/e 701,703 (M+1)+.

400 MHz $^1$H NMR (CD$_3$OD)/δ1.18 (t, J=7.6 Hz, 3H), 1.28 (t, J=7.4 Hz, 3H), 1.30 (s, 9H), 2.39 (q, J=7.6 Hz, 2H), 2.69 (q, J=7.4 Hz, 2H), 5.10 (s, 2H), 7.14–7.20 (m, 2H), 7.30–7.40 (m, 2H), 7.53–7.75 (m, 4H), 7.93 (d, J=2.5 Hz, 1H), 8.16 (dd, J=1.2, 9.2 Hz, 1H)

EXAMPLE 7

2-[2-Bromo-5-[(ethoxyacetyl)amino]phenyl]-4-[[2'-[N-(t-butoxycarbonyl)sulfamoyl]-3-fluorobiphenyl-4-yl]methyl]-2,4-dihydro -5-ethyl-3H-1,2,4-triazol-3-one Step A: 2-[2-Bromo-5-[(ethoxyacetyl)amino]phenyl]-4-[[2'-(N-t -butylsulfamoyl)-3-fluorobiphenyl-4-yl]methyl]-2,4-dihydro-5-ethyl-3H-1,2,4-triazo-3-one To a solution of 28 μL (0.299 mmol, 31 mg) of ethoxyacetic acid in 0.3 mL of dry CH$_2$Cl$_2$ was added 132 mg (0.299 mmol) of benzotriazol-1-yloxy-tris(dimethylamino)phosphonium hexafluorophosphate (BOP Reagent) and 90 mg (0.150 mmol) of 2-(5-amino-2-bromophenyl)-4-[[2'-(N-t-butylsulfamoyl)-3-fluorobiphenyl-4yl]methyl]-2,4-dihydro-5-ethyl-3H-1,2,4-triazol-3-one (from Example 1, Step H). The resulting reaction mixture was stirred overnight at room temperature. After evaporation of volatiles, the residue was taken up in ethyl acetate and washed five times with saturated NaHCO$_3$, water, and brine, and dried over anhydrous Na$_2$SO$_4$. This gave 84 mg (82%) of the desired product after filtration and removal of volatiles in vacuo. This material was homogeneous by TLC, and deemed to be of sufficient purity to be used in the next step without further purification.

400 MHz $^1$H NMR (CDCl$_3$) δ1.01 (s, 9H), 1.27 (m, 6H), 2.60 (q, J=7.4 Hz, 2H), 3.62 (m, 2H), 4.01 (s, 2H), 4.99 (s, 2H), 7.20–7.35 (m, 2H), 7.40–7.65 (m, 5H), 7.73 (s, 1H), 8.14 (dd, J=1.5, 7.9 Hz, 1H), 8.39 (s, 1H)

Step B: 2-[2-Bromo-5-[(ethoxyacetyl)amino]phenyl]-4-[[2'-[N-(t -butoxycarbonyl)sulfamoyl]-3-fluorobiphenyl-4-yl]methyl]2,4-dihydro-5-ethyl-3H-1,2,4-triazol-3-one The elaboration of 2-[2-bromo-5-[(ethoxyacetyl)amino phenyl]-4-[[2'-(N-t-butylsulfamoyl)-3-fluorobiphenyl-4yl]methyl]-2,4-dihydro-5-ethyl-3H-1,2,4-triazol-3-one (from Step A) to the titled compound was achieved via a sequence of transformations analogous to those described for Example 1, Steps J and K. After chromatographic purification, the titled compound was obtained in 74% yield, mp 132°–134° C.; mass spectrum (FAB) m/e 731,733 (M+1)+.

400 MHz $^1$H NMR (CD$_3$OD) δ1.27 (m, 6H), 1.30 (s, 9H), 2.69 (q, J=7.4 Hz, 2H), 3.64 (q, J=7.0 Hz, 2H), 4.08 (s, 2H), 5.10 (s, 2H), 7.15–7.22 (m, 2H), 7.30–7.40 (m, 2H), 7.57–7.75 (m, 4H), 7.97 (d, J=2.5 Hz, 1H), 8.16 (dd, J=1.3, 8.0 Hz, 1H)

EXAMPLE 8

2-[2-Bromo-5-(valerylamino)phenyl]-2,4-dihydro-5-ethyl-4-[[3-fluoro -2'-[N-(isopropoxycarbonyl)sulfamoyl]biphenyl-4-yl]methyl]-3H-1,2,4-triazol-3-one The titled compound was prepared from 2-[2-bromo-5-(valerylamino)phenyl]-2,4-dihydro-5-ethyl-4-[(3-fluoro-2'-sulfamoyl -biphenyl-4-yl)methyl]-3H-1,2,4-triazol-3-one (from Example 1, Step J) as described in Example 1, Step K, except that isopropyl chloroformate was used in place of di-t-butyl dicarbonate, and THF was used as the solvent. After chromatographic purification, the titled compound was obtained in 15% yield; mass spectrum (FAB) m/e 716,718 (M+1)+.

400 MHz $^1$H NMR (CD$_3$OD) δ0.95 (t, J=7.4 Hz, 3H), 1.10 (m, 6H), 1.28 (t, J=7.4 Hz, 3H), 1.40 (m, 2H), 1.65 (m, 2H), 2.38 (q, J=7.4 Hz, 2H), 2.68 (q, J=7.4 Hz, 2H), 5.10 (s, 2H), 7.13–7.20 (m, 2H), 7.30–7.40 (m, 2H), 7.537–7.75 (m, 4H), 7.93 (d, J=2.4 Hz, 1H), 8.17 (dd, J=1.4, 8.7 Hz, 1H)

EXAMPLE 9

2-[5-(Acetylamino)-2-chlorophenyl]-4-[[2'-[N-(t-butoxycarbonyl)sulfamoyl]-3-fluorobiphenyl-4-yl]methyl]-2,4-dihydro-5-ethyl-3H -1,2,4-triazol-3-one Step A: 4-[[2'-(N-t-Butylsulfamoyl)-3-fluorobiphenyl-4-yl]methyl]-2-(2-chloro-5-nitrophenyl)-2,4-dihydro-5-ethyl-3H- 1,2,4-triazol-3-one The titled compound was prepared from 2-chloro-5-nitrophenylhydrazine and 2-ketobutyric acid in a sequence of transformations analogous to those described in Example 1, Steps A through F. After chromatographic purification, the titled compound was obtained in 88% yield; mass spectrum (FAB) m/e 588 (M+1)+.

400 MHz $^1$H NMR (CDCl$_3$) δ1.01 (s, 9H), 1.29 (t, J=7.4 Hz, 3H), 2.61 (q, J=7.4 Hz, 2H), 3.68 (s, 1H), 4.99 (s, 2H), 7.20–7.33 (m, 2H), 7.40–7.65 (m, 3H), 7.66 (m, 1H), 7.98 (s, 1H), 8.13 (dd, J=1.6, 7.8 Hz, 1H), 8.18 (dd, J=1.5, 8.8 Hz, 1H), 8.37 (d, J=2.6 Hz, 1H)

Step B: 2-(2-Chloro-5-nitrophenyl)-2,4-dihydro-5-ethyl-4-[(3-fluoro-2'-sulfamoylbiphenyl-4-yl)methyl]-3H-1,2,4-triazol -3-one The titled compounct was prepared from 4-[[2'-(N-t -butylsulfamoyl)-3-fluorobiphenyl-4-yl]methyl]-2-(2-chloro-5-nitrophenyl)-2,4-dihydro-5-ethyl-3H-1,2,4-triazol-3-one (from Step A) according to the procedure of Example 1, Step J. After chromatographic purification, the titled compound was obtained in 98% yield; mass spectrum (FAB) m/e 532 (M+1)+.

400 MHz $^1$H NMR (CDCl$_3$) δ1.31 (t, J=7.4 Hz, 3H), 2.63 (q, J=7.4 Hz, 2H), 4.44 (s, 1H), 5.00 (s, 2H), 7.23–7.38 (m, 3H), 7.43 (t, J=7.7 Hz, 1H), 7.51 (t, J=7.3 Hz, 1 H), 7.60 (m, 1H), 7.67 (d, J=8.9 Hz, 1H), 8.12 (dd, J=1.2, 7.9 Hz, 1H), 8.19 (dd, J=2.6, 8.8 Hz, 1H), 8.39 (d, J=2.6 Hz, 1H)

Step C: 4-[[2'-[N-(t-Butoxycarbonyl)sulfamoyl]-3-fluorobiphenyl -4-yl]methyl]-2-(2-chloro-5-nitrophenyl)-2,4-dihydro-5-ethyl-3H-1,2,4-triazol-3-one The titled compound was prepared from 2-(2-chloro-5-nitrophenyl)-2,4-dihydro-5-ethyl-4-[(3-fluoro-2'-sulfamo ylbiphenyl-4-yl)methyl]-3H-1,2,4-triazol-3-one (from Step B) according to the procedure of Example 1, Step K. After chromatographic purification, the titled compound was obtained in 97% yield; mass spectrum (FAB) m/e 632 (M+1)+.

400 MHz $^1$H NMR (CDCl$_3$) δ1.30 (s, 9H), 1.32 (t, J=7.5 Hz, 3H), 2.64 (q, J=7.5 Hz, 2H), 5.01 (s, 2H), 7.10–7.20 (m, 2H), 7.29 (dd, J=1.4, 7.4 Hz, 1H), 7.40 (t, J=8.0 Hz, 1H), 7.55–7.62 (m, 1 H), 7.63–7.75 (m, 2H), 8.15–8.26 (m, 2H), 8.39 (d, J=2.6 Hz, 1H)

Step D: 2-(5-Amino-2-chlorophenyl)-4-[[2'-[N-(t-butoxycarbonyl) sulfamoyl]-3-fluorobiphenyl-4-yl]methyl]-2,4-dihydro-5-ethyl-3H-1,2,4-triazol-3-one The reduction of 4-[[2'-[N-(t-butoxycarbonyl)sulfamoyl]-3-fluorobiphenyl-4-yl]methyl]-2-(2-chloro-5-nitrophenyl)-2,4-dihydro-5-ethyl-3H-1,2,4-triazol-3-one (from Step C) was hydrogenated according to the procedure of Example 2, Step B, to the give the titled compound in 72% yield after chromatographic purification; mass spectrum (FAB) m/e 602 (M+1)+.

400 MHz $^1$H NMR (CDCl$_3$) δ1.29 (m, 12H), 2.60 (q, J=7.4 Hz, 2H), 4.99 (s, 2H), 6.63 (dd, J=2.7, 8.7 Hz, 1H), 6.76 (d, J=2.7 Hz, 1H), 7.05-7.20 (m, 2H), 7.23-7.40 (m, 3H), 7.50-7.70 (m, 2H), 8.24 (dd, J=1.3, 8.0 Hz, 1H)

Step E: 2-[5-(Acetylamino)-2-chlorophenyl]-4-[[2'-[N-(t-butoxycarbonyl)sulfamoyl]-3-fluorobiphenyl-4-yl]methyl]-2,4-dihydro-5-ethyl-3H-1,2,4-triazol-3-one The acylation of 2-(5-amino-2-chlorophenyl)-4-[[2'-[N-(t-butoxycarbonyl)-sulfamoyl]-3-fluorobiphenyl-4-yl]methyl]-2,4-dihydro-5-ethyl-3H-1,2,4-triazol-3-one (from Step D) was carded out according to the procedure of Example 1, Step I, to the give the titled compound in 38% yield after chromatographic purification, mp 158°-160° C.; mass spectrum (FAB) m/e 644 (M+1)+.

400 MHz $^1$H NMR (CD$_3$OD) δ1.28 (t, J=7.4 Hz, 3H), 1.30 (s, 9H), 2.13 (s, 3H), 2.69 (q, J=7.4 Hz, 2H), 5.09 (s, 2H), 7.15-7.20 (m, 2H), 7.29-7.39 (m, 2H), 7.51 (m, 1H), 7.58-7.75 (m, 3H), 7.91 (d, J=2.5 Hz, 1H), 8.15 (dd, J=1.3, 8.0 Hz, 1H)

EXAMPLE 10

4-[[2'-[N-(t-Butoxycarbonyl)sulfamoyl]-3-fluorobiphenyl-4-yl]methyl]-2-[2-chloro-5-(propionylamino)-phenyl]-2,4-dihydro-5-ethyl-3H-1,2,4-triazol-3-one The titled compound was obtained by the acylation of 2-(5-amino-2-chlorophenyl)-4-[[2'-[N-(t-butoxycarbonyl)-sulfamoyl]-3-fluorobiphenyl-4-yl]methyl]-2,4-dihydro-5-ethyl-3H-1,2,4-triazol-3-one (from Example 9, Step D) according to the procedure of Example 1, Step I. This gave the desired compound in 42% yield after chromatographic purification, mp 142°-144° C., mass spectrum (FAB) m/e 658 (M+1)+.

400 MHz $^1$H NMR (CD$_3$OD) δ1.15-1.25 (m, 6H), 1.29 (s, 9H), 2.39 (q, J=7.5 Hz, 2H), 2.69 (q, J=7.4 Hz, 2H), 5.09 (s, 2H), 7.15-7.22 (m, 2H), 7.29-7.39 (m, 2H), 7.51 (m, 1H), 7.55-7.73 (m, 3H), 7.91 (d, J=2.6 Hz, 1H), 8.15 (dd, J=1.3, 8.0 Hz, 1H)

EXAMPLE 11

2-[5-(Benzoylamino)-2-chlorophenyl]-4-[[2'-[N-(t-butoxycarbonyl)sulfamoyl]-3-fluorobiphenyl-4-yl]methyl]-2,4-dihydro-5-ethyl-3H -1,2,4-triazol-3-one The titled compound was obtained by the acylation of 2-(5-amino-2-chlorophenyl)-4-[[2'-[N-(t-butoxycarbonyl)-sulfamoyl]-3-fluorobiphenyl-4-yl]methyl]-2,4-dihydro-5-ethyl-3H-1,2,4-triazol-3-one (from Example 9, Step D) according to the procedure of Example 1, Step I. This gave the desired compound in 34% yield after chromatographic purification, mp 79°-81° C.; mass spectrum (FAB) m/e 706 (M+1)+.

400 MHz $^1$H NMR (CD$_3$OD) δ1.30 )m, 12H), 2.70 (q, J=7.4 Hz, 2H), 5.11 (s, 2H), 7.15-7.22 (m, 2H), 7.30-7.40 (m, 2H), 7.40-7.48 (m, 2H), 7.49-7.72 (m, 6H), 7.80-8.20 (m, 5H)

EXAMPLE 12

4-[[2'-[N-(t-Butoxycarbonyl)sulfamoyl]-3-fluorobiphenyl-4-yl]methyl]-2-[2-chloro-5-(valerylamino )phenyl]-2,4-dihydro-5-ethyl-3H-1,2,4-triazol-3-one Step A: 2-[2-Chloro-5-(valerylamino)phenyl]-2,4-dihydro-5-ethyl -4-[(3-fluoro-2'-sulfamoylbiphenyl-4-yl)methyl]-3H-1,2,4-triazol-3-one The titled compound was prepared staffing from from 2-chloro-5-nitrophenylhydrazine and 2-ketobutyric acid in a sequence analogous to those described for Example 1, Steps A-J. After chromatographic purification, the titled compound was obtained in 74% yield as a cream-colored solid, homogeneous by TLC (19:1 CH$_2$Cl$_2$:MeOH), mass spectrum (FAB) m/e 586 (M+1)+.

400 MHz $^1$H NMR (CDCl$_3$) δ50.90 (t, J=7.4 Hz, 3H), 1.28 (t, J=7.5 Hz, 3H), 1.35 (m, 2H), 1.63 (m, 2H), 2.30 (m, 2H), 2.58 (q, J=7.5 Hz, 2H), 4.45 (s, 2H), 5.00 (s, 2H), 7.20-7.45 (m, 4H), 7.45-7.75 (m, 5H), 8.15 (dd, J=1.4, 7.8 Hz, 1H)

Step B: 4-[[2'-[N-(t-Butoxycarbonyl)sulfamoyl]-3-fluorobiphenyl -4-yl]methyl]-2-[2-chloro-5-(valerylamino)phenyl]-2,4-dihydro-5-ethyl-3H-1,2,4-triazol-3-one The titled compound was obtained by treating 2-[2-chloro -5-(valerylamino)phenyl]-2,4-dihydro-5-ethyl-4-[(3-fluoro-2'-sulfamoylbiphenyl-4-yl)methyl]-3H-1,2,4-triazol-3-one (from Step A) with di-t-butyl dicarbonate and NaH in THF as described in Example 1, Step K. This gave the desired compound in 78% yield after chromatographic purification, mp 143°-145° C.; mass spectrum (FAB) m/e 686 (M+1)+.

Analysis for C$_{33}$H$_{37}$ClFN$_5$O$_6$S.O0.16CH$_2$Cl$_2$ (C, H, N) Calcd C, 57.76; H, 5.44; N, 10.21. Found C, 56.88; H, 5.32, N, 9.94.

400 MHz $^1$H NMR (CD$_3$OD) δ0.92 (t, J=7.4 Hz, 3H), 1.28 (t, J=7.5 Hz, 3H), 1.30 (s, 9H), 1.40 (m, 2H), 1.66 (m, 2H), 2.36 (q, J=7.4 Hz, 2H), 2.69 (q, J=7.5 Hz, 2H), 5.09 (s, 2H), 7.13-7.22 (m, 2H), 7.29-7.39 (m, 2H), 7.50 (m, 1H), 7.57-7.73 (m, 3H), 7.93 (d, J=2.5 Hz, 1H), 8.16 (dd, J=1.3, 8.0 Hz, 1H)

EXAMPLE 13

4-[[2'-[N-(t-Butoxycarbonyl)sulfamoyl]-3-fluorobiphenyl-4-yl]methyl]-2-[2-chloro-5-[(ethoxyacetyl)amino]phenyl]-2,4-dihydro-5-ethyl-3H -1,2,4-triazol-3-one The titled compound was obtained by treating 2-[2-chloro -5-[(ethoxyacetyl)amino}phenyl]-2,4-dihydro-5-ethyl-4-[(3-fluoro-2'-sulfamoylbiphenyl-4-yl)methyl]-3H-1,2,4-triazol-3-one(prepared from the corresponding aniline and ethoxyacetic acid according to the procedure of Example 7, Step A) with di-t-butyl dicarbonate and NaH in THF as described in Example 1, Step K. This gave the desired compound in 66% yield after chromatographic purification, mp 140°-142° C.; mass spectrum (FAB) m/e 688 (M+1)+.

Analysis for C$_{33}$H$_{37}$ClFN$_5$O$_6$S.0.25CH$_2$Cl$_2$ (C, H, N) Calcd C, 54.60; H, 5.04; N, 9.87. Found C, 54.72; H, 4.99, N, 9.72.

400 MHz $^1$H NMR (CD$_3$OD) δ1.28 (m, 6H), 1.30 (s, 9H), 1.40 (m, 2H), 1.66 (m, 2H), 2.69 (q, J=7.4 Hz, 2H), 3.64 (q, J=7.0 Hz, 2H), 5.10 (s, 2H), 7.13-7.22 (m, 2H), 7.29-7.39 (m, 2H), 7.54 (m, 1H), 7.59-7.75 (m, 3H), 7.97 (d, J=2.5 Hz, 1H), 8.16 (dd, J=1.3, 7.9 Hz, 1H)

EXAMPLE 14

4-[[2'-[N-(t-Butoxycarbonyl)sulfamoyl]-3-fluorobiphenyl-4-yl]methyl]-2-[2-chloro-5-[(3-methoxypropionyl)amino]phenyl]-2,4-dihydro-5-ethyl-3H-1,2,4-triazol-3-one The titled compound was obtained by treating 2-[2-chloro -5-[(3-methoxypropionyl)amino]phenyl]-2,4-dihydro-5-ethyl-4-[(3-fluoro-2'-sulfamoylbiphenyl-4-yl)methyl]-3H-1,2,4-triazol-3-one (prepared in a reaction analogous to Example 7, Step A, using 3-methoxypropionic acid) with di-t-butyl dicarbonate and NaH in THF as described in Example 1, Step K. This gave the desired compound in 49% yield after chromatographic purification, mp 128°–131° C.; mass spectrum (FAB) m/e 701 (M+2Li)+.

400 MHz $^1$H NMR (CD$_3$OD) δ1.28 (t, J=7.5 Hz, 3H), 1.30 (s, 9H), 2.61 (t, J=6.1 Hz, 2H), 2.69 (q, J=7.5 Hz, 2H), 3.34 (s, 3H), 3.71 (t, J =6.1 Hz, 2H), 5.10 (s, 2H), 7.13–7.22 (m, 2H), 7.30–7.40 (m, 2H), 7.51 (m, 1H), 7.59–7.75 (m, 3H), 7.94 (d, J=2.5 Hz, 1H), 8.16 (dd, J=1.2, 7.9 Hz, 1H)

EXAMPLE 15

2-[2-Bromo-5-(valerylamino)phenyl]-4-[[2′-[N-(t-butoxycarbonyl)sulfamoyl]-3-fluorobiphenyl-4-yl]methyl]-2,4-dihydro-5-methyl-3H-1,2,4-triazol-3-one The titled compound was obtained in 10 steps starting from 2-bromo-5-nitrophenylhydrazine and pyruvic acid as described in Example 1 for the 5-ethyl analogue. In the final step the desired material was obtained in 57% yield after chromatographic purification, mp 140°–142° C.; mass spectrum (FAB) m/e 716,718 (M+1)+.

400 MHz $^1$H NMR (CD$_3$OD) δ0.95 (t, J=7.4 Hz, 3H), 1.30 (s, 9H), 1.40 (m, 2H), 1.66 (m, 2H), 2.33 (s,3H), 2.36 (q, J=7.4 Hz, 2H), 5.09 (s, 2H), 7.13–7.20 (m, 2H), 7.33–7.39 (m, 2H), 7.54 (m, 1H), 7.59–7.75 (m, 3H), 7.93 (d, J=2.5 Hz, 1H), 8.16 (dd, J=1.3, 8.1 Hz, 1H)

What is claimed is:

1. A compound structural formula (I):

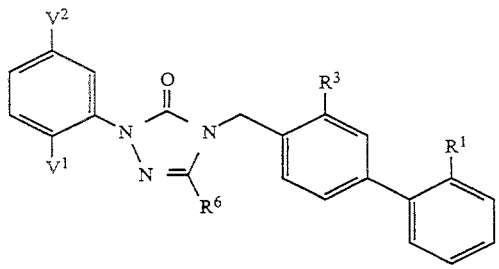

or a pharmaceutically acceptable salt thereof, wherein:
R$^1$ is —SO$_2$NHCO$_2$R$^{22}$, wherein R$^{22}$ is branched chain C$_3$–C$_4$ alkyl;
R$^3$ is Cl, Br, I, or F;
R$^6$ is straight chain C$_1$–C$_2$ alkyl;
V$^1$ is Cl, Br, or CF$_3$;
V$_2$ is
(a) —(CH$_2$)$_t$NR$^{21}$COR$^{22}$, wherein t is 0; R$^{21}$ is H; and R$^{22}$ is phenyl, C$_1$–C$_4$ alkyl or C$_1$–C$_2$ alkyl substituted with methoxy or ethoxy; or
(b) —CONR$^{21}$R$^{22}$, wherein R$^{21}$ is H; and R$^{22}$ is C$_1$–C$_4$ alkyl.

2. The compound of Formula I as recited in claim 1, or a pharmaceutically acceptable salt thereof, wherein:
R$^1$ is —SO$_2$NHCO$_2$R$^{22}$, wherein R$^{22}$ is isopropyl or tert-butyl;
R$^3$ F;
R$^6$ is C$_1$–C$_2$ alkyl;
V$^1$ is Cl, Br, or CF$_3$;
V$^2$ is
(a) —NHCOR$^{22}$, wherein R$^{22}$ is phenyl, C$_1$–C$_4$ alkyl or C$_1$–C$_2$ alkyl substituted with methoxy or ethoxy; or
(b) —CONHR$_{22}$, wherein R$^{22}$ is C$_1$–C$_4$ alkyl.

3. The compound of claim 1 of structural formula (I):

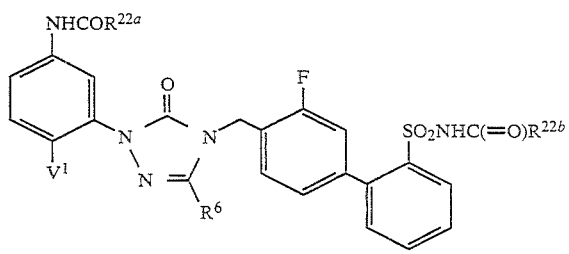

wherein the substituents are as recited in the table below:

| R$^{22a}$ | R$^6$ | V$^1$ | R$^{22b}$ |
|---|---|---|---|
| phenyl | ethyl | Br | O-t-butyl |
| ethyl | ethyl | Br | O-t-butyl |
| n-butyl | ethyl | Br | O-t-butyl |
| ethyl | ethyl | Cl | O-t-butyl |
| methyl | ethyl | Cl | O-t-butyl |
| phenyl | ethyl | Cl | O-t-butyl |
| ethoxymethyl | ethyl | Br | O-t-butyl |
| ethoxymethyl | ethyl | Cl | O-t-butyl |
| n-butyl | ethyl | Cl | O-t-butyl |
| 2-methoxyethyl | ethyl | Br | O-t-butyl |
| n-butyl | ethyl | Br | O-i-propyl |
| n-butyl | ethyl | CF$_3$ | O-t-butyl |
| n-butyl | methyl | Br | O-t-butyl. |

4. The compound of claim 1 of the structural formula I:

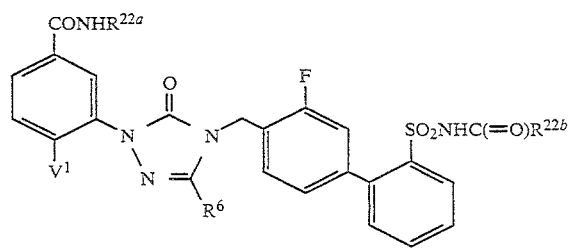

wherein the substituents are as recited in the table below:

| R$^{22a}$ | R$^6$ | V$^1$ | R$^{22b}$ |
|---|---|---|---|
| n-butyl | ethyl | CF$_3$ | O-t-butyl |
| n-butyl | ethyl | Br | O-t-butyl |
| ethyl | ethyl | Br | O-t-butyl |
| ethyl | ethyl | Cl | O-t-butyl |
| methyl | ethyl | Cl | O-t-butyl |
| n-butyl | ethyl | Cl | O-t-butyl |
| n-butyl | ethyl | Br | O-i-propyl |
| n-butyl | methyl | Br | O-t-butyl. |

5. A compound of formula I which is 2-[4-bromo-5-(valerylamino)phenyl]-4-[[2'-[N-(t-butoxycarbonyl)sulfamoyl]-3-fluoro-biphenyl-4-yl]methyl]-2,4-dihydro-5-ethyl-3H-1,2,4-triazol-3-one or a pharmaceutically acceptable salt thereof.

6. A pharmaceutical composition useful in the treatment of hypertension which comprises a pharmaceutically acceptable carrier and a pharmaceutically effective amount of a compound of claim 1.

* * * * *